US009462963B2

(12) United States Patent
Salamitou

(10) Patent No.: US 9,462,963 B2
(45) Date of Patent: Oct. 11, 2016

(54) RESPIRATION MONITORING

(75) Inventor: Philipe Salamitou, Boulogne Billancourt (FR)

(73) Assignee: SRETT, Boulogne-Billancourt (FR)

( * ) Notice: Subject to any disclaimer, the term of this patent is extended or adjusted under 35 U.S.C. 154(b) by 1000 days.

(21) Appl. No.: 13/512,335

(22) PCT Filed: Dec. 1, 2010

(86) PCT No.: PCT/EP2010/068671
§ 371 (c)(1),
(2), (4) Date: May 27, 2012

(87) PCT Pub. No.: WO2011/067300
PCT Pub. Date: Jun. 9, 2011

(65) Prior Publication Data
US 2012/0232420 A1 Sep. 13, 2012

(30) Foreign Application Priority Data

Dec. 2, 2009 (EP) ..................................... 09306170

(51) Int. Cl.
*A61B 5/08* (2006.01)
*A62B 9/00* (2006.01)
(Continued)

(52) U.S. Cl.
CPC ............. *A61B 5/087* (2013.01); *A61B 5/4818* (2013.01); *A61M 16/00* (2013.01);
(Continued)

(58) Field of Classification Search
USPC .................... 600/538; 128/204.25, 204.18
See application file for complete search history.

(56) References Cited

U.S. PATENT DOCUMENTS 3,838,598 A * 10/1974 Tompkins ................. G01F 1/42
73/861.52
4,198,860 A * 4/1980 King .............................. 73/195
(Continued)

FOREIGN PATENT DOCUMENTS

EP 0552916 A1 7/1993
EP 0815792 A1 1/1998
(Continued)

OTHER PUBLICATIONS

Dehoney, R. W., "Construction and Testing of a Laboratory Fluid Flow Apparatus" University of Louisville, (1936) (Dehoney).*
(Continued)

*Primary Examiner* — Michael Kahelin
*Assistant Examiner* — Mitchell E Alter
(74) *Attorney, Agent, or Firm* — The Jansson Firm; Pehr B. Jansson

(57) ABSTRACT (EN) Respiration of a patient can be monitored by means of a device (ASD) that has the following characteristics. An inlet (IL) receives a pressurized airflow of breathable air from an airflow source. An outlet (OL) applies the pressurized airflow to a mask worn by the patient. An airflow path (AFP) is arranged between the inlet (IL) and the outlet (OL). The airflow path (AFP) has an axis (AX) and exhibits a decrease ($-\Delta D$) in diameter followed by an increase ($+\Delta D$) in diameter in a direction from the inlet (IL) to the outlet (OL). The increase ($+\Delta D$) in diameter comprises an initial portion (WI) in which the diameter increases according to a slope ($\phi$) of less than 10° with respect to the axis (AX). A pressure measurement arrangement (PS1, PS2) provides an indication (SO) of a pressure difference in the pressurized airflow between two sections (IN, T) of the airflow path that have different diameters.

15 Claims, 5 Drawing Sheets

(51) Int. Cl.
*A61B 5/087* (2006.01)
*A61B 5/00* (2006.01)
*A61M 16/00* (2006.01)
*G01F 1/36* (2006.01)
*G01F 1/44* (2006.01)
*A61M 16/06* (2006.01)

(52) U.S. Cl.
CPC ......... *A61M 16/0051* (2013.01); *G01F 1/363* (2013.01); *G01F 1/44* (2013.01); *A61M 16/06* (2013.01); *A61M 2016/0036* (2013.01); *A61M 2205/15* (2013.01); *A61M 2205/8212* (2013.01)

(56) References Cited

U.S. PATENT DOCUMENTS

| | | | | |
|---|---|---|---|---|
| 4,265,237 | A | * | 5/1981 | Schwanbom ......... A61M 16/00 128/204.24 |
| 6,105,575 | A | * | 8/2000 | Estes et al. .............. 128/204.23 |
| 6,224,560 | B1 | * | 5/2001 | Gazula et al. ................. 600/538 |
| 2001/0004893 | A1 | * | 6/2001 | Biondi .................. A61M 16/00 128/204.18 |
| 2002/0069022 | A1 | * | 6/2002 | Fincke ........................... 702/45 |
| 2002/0139197 | A1 | * | 10/2002 | Salamitou ................. G01F 1/74 73/861.04 |
| 2004/0167419 | A1 | | 8/2004 | Fathollahzadeh |
| 2005/0121033 | A1 | * | 6/2005 | Starr et al. ................ 128/204.18 |
| 2010/0036266 | A1 | * | 2/2010 | Myklebust et al. .......... 600/500 |
| 2010/0191481 | A1 | * | 7/2010 | Steven ........................... 702/47 |

FOREIGN PATENT DOCUMENTS

| | | |
|---|---|---|
| GB | 2267758 A | 12/1993 |
| WO | WO9943388 A1 | 9/1999 |
| WO | WO9945989 A1 | 9/1999 |
| WO | WO 2008/025935 A1 * | 3/2008 |

OTHER PUBLICATIONS

PCT/EP2010/068671, International Search Report, Jan. 7, 2011, European Patent Office, P.B. 5818 Patentlaan 2 NL—2260 HV Rijswijk.

* cited by examiner

RESPIRATION MONITORING

FIELD OF THE INVENTION

An aspect of the invention relates to a device for monitoring respiration of a patient. The device may be used, for example, to detect respiratory disorders, such as hypopnea and apnea. Other aspects of the invention relate to a system for monitoring respiration of a patient and a method of such monitoring.

BACKGROUND OF THE INVENTION

A technique referred to as "positive airway pressure" (PAP) allows monitoring respiration of a patient who suffers from respiratory disorders, such as, for example, apnea or hypopnea. In accordance with this technique, the patient receives a pressurized airflow via a mask, preferably while the patient is asleep. An airflow source, which is typically in the form of a ventilation unit, produces the pressurized airflow. The pressurized airflow typically comprises breathable air, which may optionally be oxygen-enriched, or have any other suitable composition. The airflow source is adjusted in accordance with an airflow pressure that a physician has prescribed. An airflow sensing device is coupled between the airflow source and the mask. The airflow sensing device provides an indication of a rate at which the airflow traverses the airflow sensing device. A processor may produce monitoring data on the basis of the indication that the airflow sensing device provides.

WO 9945989 describes a system for treatment of a medical disorder such as obstructive sleep apnea or congestive heart failure. The system comprises a flow sensor that determines a flow rate of pressurized gas delivered to a patient. The system delivers a pressure to the patient that is a function of this patient flow rate.

SUMMARY OF THE INVENTION

There is a need for a solution that allows relatively precise respiration monitoring in a wide variety of monitoring contexts. In order to better address this need, the following aspects have been taken into consideration.

A physician typically prescribes a given pressure for an airflow that is to be applied to a patient who has a respiratory problem. This given pressure preferably corresponds to a minimally required pressure to address the patient's respiratory problem. This is because the greater the pressure of the airflow is, the more discomfort this generally causes for the patient. A non-physician typically adjusts the airflow source such that the pressure is that prescribed by the physician.

In case an airflow sensing device that introduces a pressure loss is coupled between the airflow source and a mask worn by the patient, the pressure of the airflow delivered to the patient will not correspond to that prescribed by the physician. In principle, it would be possible to somewhat compensate for the pressure loss, by adjusting the airflow source to a pressure higher than that prescribed by the physician. However, this is not a practical and reliable solution. The non-physician, who adjusts the airflow source, may not be aware that an airflow sensing device will be used, or may not be certain about this. Even if the non-physician knows that an airflow sensing device will be used, he or she may not know the pressure loss this device will introduce, or may not be certain about this. What is more, the pressure loss will vary as a function of the patient breathing in and breathing out. The pressure loss is not constant and can therefore not be compensated in a precise manner by offsetting the pressure of the airflow source.

In accordance with an aspect of the invention, a device for monitoring respiration of a patient comprises:

an inlet for receiving a pressurized airflow from an airflow source;

an outlet for applying the pressurized airflow to a mask that can be worn by the patient;

an airflow path arranged between the inlet and the outlet, the airflow path having an axis and exhibiting a decrease in diameter followed by an increase in diameter in a direction from the inlet to the outlet, whereby the increase in diameter comprises an initial portion in which the diameter increases according to a slope of less than 10° with respect to the axis, the initial portion accounting for at least two thirds of the increase in diameter; and a pressure measurement arrangement arranged to provide an indication of a pressure difference in the pressurized airflow between two sections of the airflow path that have different diameters; and a processing module arranged to determine a variation of a respiratory parameter over time on the basis successive indications of pressure differences that the pressure measurement arrangement provides.

In such a device, the pressurized airflow can traverse the airflow path without any substantial pressure loss. The airflow path thus introduces only an insignificant pressure loss when inserted between an airflow source and a mask worn by a patient. For example, a pressure loss of only 20 Pa can be achieved for an airflow that has a flow rate of 1 liter per second. The airflow source therefore can simply be adjusted to provide the pressure prescribed by a physician, without any need to compensate for a pressure loss that could lead to errors.

It is important to note that the indication of the pressure difference, which the device in accordance with the invention provides, constitutes a relatively imprecise indication of instantaneous flow rate in positive airway pressure (PAP) applications. This is because, in PAP applications, the airflow path in accordance with the invention has a relatively large inner diameter and flow rates are relatively low. For example, an inner diameter is typically 22 mm and flow rates are typically in a range between 0 and 1 liter per second, with an average flow rate of approximately 0.5 liter per second. As a result, the airflow path provides a so-called Reynolds number that is relatively low. The lower the Reynolds number is, the less precise instantaneous flow rate can be measured from pressure differences in the airflow path. Calibration cannot resolve this. In spirometry applications, flow rates are significantly higher than in PAP applications. Therefore, in spirometry applications, an airflow path in accordance with the invention might provide a Reynolds number that is sufficiently high for measuring instantaneous flow rate with acceptable precision. However, the present invention concerns PAP applications, which imply an inherent imprecision of flow rate measurement.

In PAP applications, a device in accordance with the invention can provide sufficiently precise data regarding variations of a respiratory parameter over time, despite the inherent imprecision of flow rate measurement. This is because imprecision is primarily related to a particular physical configuration and disposition of respective elements that conduct the pressurized airflow from the airflow source to the patient. The imprecision is substantially of a static nature rather than of a dynamic nature. Similar patient breathing cycles generate similar indications of pressure differences. Variations in indications of pressure differences will relatively precisely reflect variations in the breathing cycles. Therefore, respiratory disorders, such as an apnea and hypopnea, can reliably be detected by monitoring these variations over time.

In accordance with another aspect of the invention, a system for monitoring respiration of a patient comprises a device as defined hereinbefore.

In accordance with yet another aspect of the invention, a method of monitoring respiration of a patient comprises:
 a monitoring preparation step in which an inlet of an airflow sensing device is coupled to an airflow source arranged to provide a pressurized airflow, and in which an outlet is coupled to a mask for applying the pressurized airflow to the patient; the airflow sensing device comprising:
  an airflow path arranged between the inlet and the outlet, the airflow path having an axis and exhibiting a decrease in diameter followed by an increase in diameter in a direction from the inlet to the outlet, whereby the increase in diameter comprises an initial portion in which the diameter increases according to a slope of less than 10° with respect to the axis, the initial portion accounting for at least two thirds of the increase in diameter; and
  a pressure measurement arrangement arranged to provide an indication of a pressure difference in the pressurized airflow between two sections of the airflow path that have different diameters; and
 a monitoring execution step in which a variation of a respiratory parameter over time is determined on the basis successive indications of pressure differences that the pressure measurement arrangement provides.

In accordance with yet another aspect of the invention, a computer program product comprises a set of instructions that enables a processor to carry out the method identified hereinbefore.

An implementation of the invention advantageously comprises one or more of the following additional features, which are described in separate paragraphs. These additional features each contribute to achieving relatively precise respiration monitoring.

The airflow path may have a diameter profile that corresponds to that of a Venturi tube.

The increase in diameter may comprise a steep portion after the initial portion. This allows the airflow path to be relatively short.

The airflow path preferably comprises a section of constant diameter between the decrease in diameter and the increase in diameter.

The section of constant diameter preferably has a length corresponding to the constant diameter.

The pressure measurement arrangement preferably provides an indication of the pressure difference in the pressurized airflow between the section of constant diameter and an input section located before the decrease in diameter.

The pressure measurement arrangement preferably comprises a first pressure sensor at the input section located before the decrease in diameter, and a second pressure sensor located at the section of constant diameter. An indication of the pressure of the pressurized airflow at the mask can be obtained by means of the first pressure sensor.

The processing module may determine an estimation of a volume of air breathed by the patient on the basis of successive indications provided by the pressure measurement arrangement.

The processing module preferably determines an estimation of the flow rate of air breathed by the patient on the basis of the indication provided by pressure measurement arrangement. The processor then applies an integration operation to successive estimations of flow rate of air breathed by the patient so as to obtain the estimation of the volume of air breathed by the patient. It is to be noted that the integration operation acts as a low pass filter which smoothes out random variations due to noise in successive indications provided by pressure measurement arrangement. Therefore, the estimation of the volume of air breathed by the patient is relatively noise free.

The processing module may apply a square root function to the indication provided by the pressure measurement arrangement so as to determine an estimation of the flow rate of the pressurized airflow through the device. The processor estimates a flow rate of air that leaks from the mask and subtracts this estimation from the estimation of the flow rate of the pressurized airflow through the device so as to determine the estimation of the flow rate of air breathed by the patient.

The processing module may divide an average of the estimation of the flow rate of the pressurized airflow through the device by an average of the square root of a difference between an estimated pressure at the mask and an ambient pressure. This division provides a mask leak coefficient that is multiplied by the square root of a difference between an estimated pressure at the mask and an ambient pressure. This multiplication provides an estimation of a flow rate of air that leaks from the mask.

A system in accordance with the invention may comprise an auxiliary pressure measurement arrangement arranged to provide an indication of the ambient pressure.

The processing module may determine a difference between a maximum and a minimum of the estimation of the volume of air breathed by the patient in a breathing cycle. The difference represents an estimation of a tidal volume of the breathing cycle. The processor then determines changes in successive estimations of tidal volumes of successive breathing cycles so as to detect the least one of the following: hypopnea and apnea.

A detailed description, with reference to drawings, illustrates the invention summarized hereinbefore as well as the additional features.

DETAILED DESCRIPTION

Figure 1:
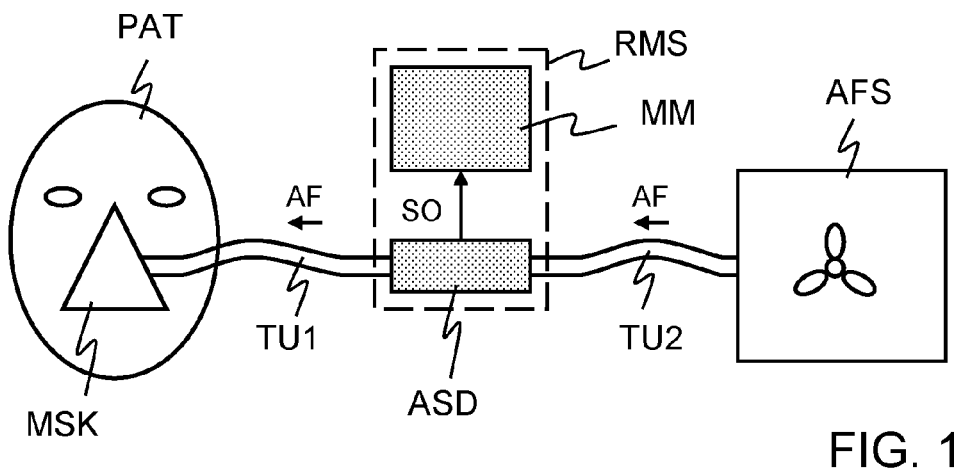
FIG. 1 is a schematic diagram that illustrates a respiration monitoring system.

FIG. 1 illustrates an application of a respiration monitoring system RMS. The respiration monitoring system RMS comprises an airflow sensing device ASD and a monitoring module MM. The airflow sensing device ASD is coupled between an airflow source AFS and a mask MSK via several tubes TU1, TU2. The mask MSK is worn by a patient PAT whose respiration needs to be monitored. The airflow source AFS is typically a ventilation unit for mechanically assisted breathing. The airflow source AFS may be of the CPAP type or the BiPAP type; CPAP is an acronym for Continuous Positive Airway Pressure; BiPAP is an acronym for Bi-level Positive Airway Pressure.

The respiration monitoring system RMS basically operates as follows. The airflow source AFS provides an airflow AF that reaches the mask MSK via the airflow sensing device ASD and the tubes TU1, TU2. The airflow AF typically comprises breathable air, which may optionally be oxygen-enriched, or have any other suitable composition. The airflow AF is pressurized. That is, the airflow source AFS provides the airflow AF at a pressure that is higher than an ambient pressure at a location where the respiration monitoring system RMS is applied.

The patient PAT breathes via the mask MSK. The mask MSK has a predefined air leakage capacity; a portion of the airflow AF leaks to the ambient air. This, and the fact that the airflow AF is pressurized, causes the airflow AF to have a flow rate that fluctuates as a function of the patient PAT breathing in and breathing out. The flow rate will typically be comprised in a range between 0 and 1 liter per second, with an average of approximately 0.5 liter per second. This is because the respiration monitoring system RMS will typically be monitoring respiration while the patient is asleep.

The airflow sensing device ASD provides an output signal pair SO that is indicative of the flow rate. The monitoring module MM monitors variations of at least one respiratory parameter of the patient PAT over time on the basis of this output signal pair SO. For example, the monitoring module MM may reliably detect hypopnea or apnea events, or both, and provide statistical data on these events. This is despite the facts that the output signal pair SO will typically indicate the flow rate with a relatively poor precision and that the output signal pair SO may be relatively noisy.

Figure 2:
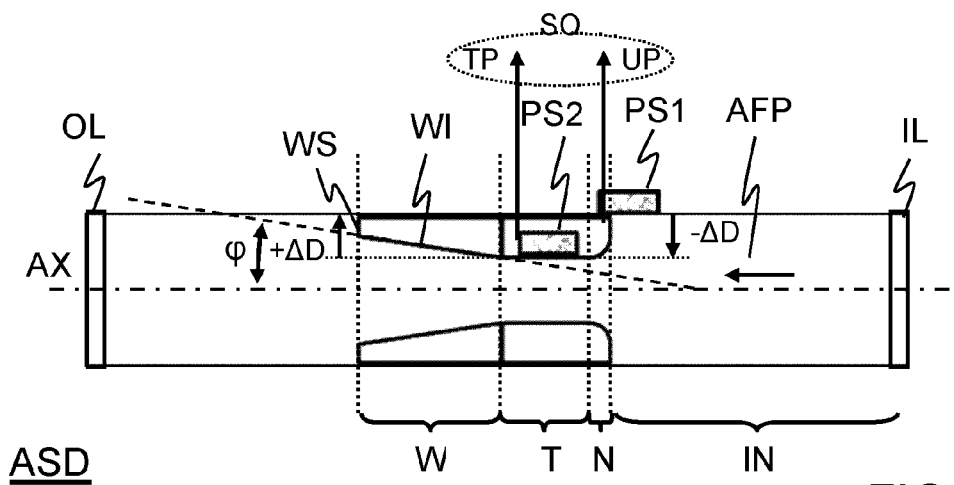
FIG. 2 is a schematic diagram that illustrates an airflow sensing device that forms part of the respiration monitoring system.

FIG. 2 schematically illustrates the airflow sensing device ASD. The airflow sensing device ASD comprises an inlet IL, an outlet OL, and an airflow path AFP arranged between the inlet IL and the outlet OL. The inlet IL and the outlet O may have an inner diameter of, for example, 18 millimeter. The airflow path AFP has an axis AX as indicated in FIG. 2. The airflow sensing device ASD further comprises two pressure sensors PS1, PS2.

The airflow path AFP has a particular diameter profile in a direction from the inlet IL to the outlet OL. The airflow path AFP exhibits a decrease $-\Delta D$ in diameter in a narrowing section N of the airflow path AFP. The narrowing section N illustrated in FIG. 2 has a convex inner shape and a truncated end near the inlet IL. The decrease $-\Delta D$ in diameter is therefore initially steep and then gradually lessens. This corresponds to a negative edge followed by a rounded portion in the diameter profile.

The narrowing section N is followed by a throat section T of constant diameter. The throat section T accounts for a flat portion in the diameter profile. The throat section T preferably has a length that corresponds to the constant diameter. The constant diameter may be, for example, 10 millimeter.

The airflow path AFP exhibits an increase $+\Delta D$ in diameter in a widening section W of the airflow path AFP, which follows the throat section T. The widening section W illustrated in FIG. 2 has a cone-like inner shape and a truncated end near the outlet OL. The increase $+\Delta D$ in diameter thus comprises an initial portion WI, wherein the increase is gradual, followed by a steep portion WS.

In the initial portion WI, the diameter preferably increases according to a slope $\phi$ of less than 10° with respect to the axis AX. This thus corresponds to a similar positive slope in the diameter profile. The initial portion WI preferably accounts for at least two thirds of the increase $+\Delta D$ in diameter. Consequently, the steep portion WS of the increase in diameter accounts for less than one third of the increase $+\Delta D$ in diameter. These characteristics allow the airflow AF to traverse the airflow path AFP without any substantial pressure loss. The airflow sensing device ASD thus introduces only an insignificant pressure loss.

As to the two pressure sensors PS1, PS2, one is located at an input section IN before the narrowing section N, that is, before the decrease $-\Delta D$ in diameter. This pressure sensor will be referred to as upstream pressure sensor PS1 hereinafter. The other pressure sensor is located at the throat section T of constant diameter. This pressure sensor will be referred to as throat pressure sensor PS2 hereinafter. The pressure sensors PS1, PS2 preferably have a resolution in the order of a few Pascal.

The airflow sensing device ASD basically operates as follows. The decrease $-\Delta D$ in diameter of the airflow path AFP, which occurs in the narrowing section N, causes a local pressure drop in the airflow AF that traverses the airflow path AFP. That is, the airflow AF has a pressure in the throat section T that is lower than the pressure in the input section IN. The pressure in the throat section T will be referred to as throat pressure hereinafter. The pressure in the input section IN will be referred to as upstream pressure hereinafter. The higher the flow rate of the airflow AF is, the greater the difference is between the upstream pressure and the throat pressure.

The upstream pressure sensor PS1 provides an output signal UP that represents the upstream pressure. This output signal will be referred to as upstream pressure signal UP hereinafter. The throat pressure sensor PS2 provides an output signal TP that represents the pressure of the airflow AF in the throat section T. This output signal will be referred to as throat pressure signal TP hereinafter.

Since the difference between the upstream pressure and the throat pressure varies as a function of the flow rate, the upstream pressure signal UP and the throat pressure signal TP form the aforementioned output signal pair SO that provides an indication of the flow rate. It should be noted that the upstream pressure signal UP also represents a pressure of the airflow AF at the mask MSK. This is because the airflow path AFP does not introduce any significant pressure loss.

However, the airflow path AFP illustrated in FIG. 2 and described hereinbefore provides a relatively low Reynolds number in the range of flow rates between 0 and 1 liter per second. As a result, the indication of the flow rate that the output signal pair SO provides is relatively imprecise. Moreover, the indication may be relatively noisy. This is because the indication is derived from a difference between the upstream pressure signal UP and the throat pressure signal TP. The difference will be relatively small whereas noise components in the aforementioned signals add up.

Figure 3:
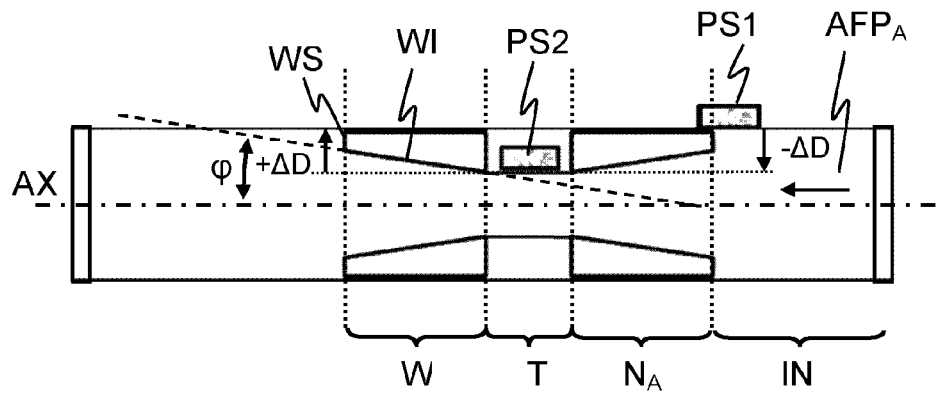
FIG. 3 is a schematic diagram that illustrates an alternative to an airflow path within the airflow sensing device.

FIG. 3 illustrates an alternative airflow path $AFP_A$ arranged between the inlet IL and the outlet OL and with the axis AX. The alternative airflow path $AFP_A$ comprises an alternative narrowing section $N_A$. As a result, the alternative airflow path $AFP_A$ exhibits a decrease $-\Delta D$ in diameter that is shaped differently with respect to that of the airflow path AFP illustrated in FIG. 2. The alternative airflow path $AFP_A$ may have a throat section T and a widening section W identical to those of the airflow path AFP illustrated in FIG. 2. The upstream pressure sensor PS1 and the throat pressure sensor PS2 are arranged with respect to the alternative airflow path $AFP_A$ as indicated in FIG. 3.

The alternative narrowing section $N_A$ has a cone-like inner shape and a truncated end near the inlet IL. The decrease $-\Delta D$ in diameter thus has an initial steep portion WS followed by a relatively long gradual portion. In this gradual portion, the diameter increases according to a slope comprised between, for example, 5° and 45° with respect to the axis AX. This corresponds to a similar negative slope $\phi$ in the diameter profile. The alternative narrowing section $N_A$ may be symmetrical with respect to the widening section W, in which case the aforementioned slope will be less than 10°. The alternative airflow path $AFP_A$ may thus have a diameter profile that corresponds to that of a Venturi tube.

Figure 4:
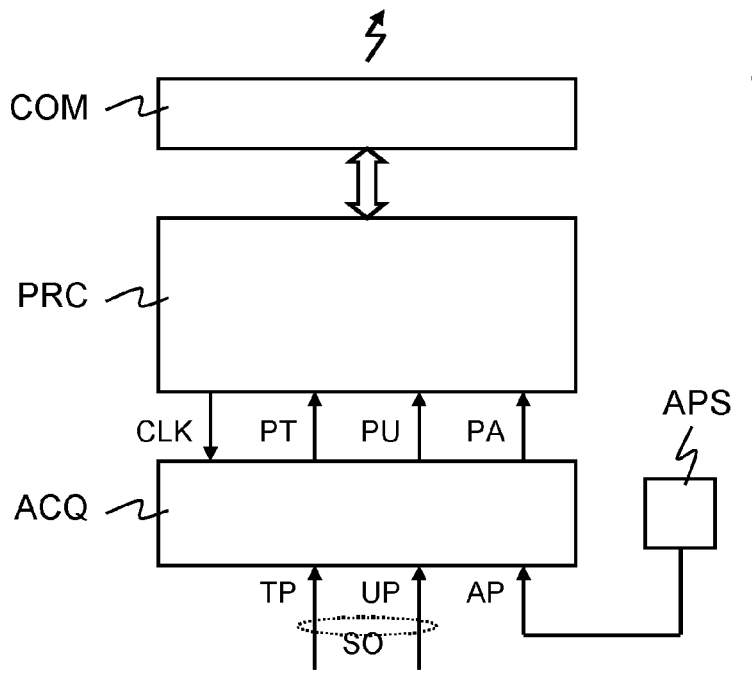
FIG. 4 is a block diagram that illustrates a monitoring module that forms part of the respiration monitoring system.

FIG. 4 illustrates the monitoring module MM. The monitoring module MM comprises a processor PRC, a data acquisition interface ACQ, a data communication interface COM, and an ambient pressure sensor APS. The processor PRC may comprise a program memory, in which instructions have been stored, and a module for executing these instructions. In such a software-based implementation, the set of instructions defines various operations that the monitoring module MM carries out, which will be described in greater detail hereinafter The data acquisition interface ACQ may comprise, for example, one or more analog-to-digital converters. The data communication interface COM may comprise, for example, a wireless link module, or a USB module, or both. The monitoring module MM can be battery operated.

The monitoring module MM basically operates as follows. The data acquisition interface ACQ receives the upstream pressure signal UP and the throat pressure signal TP, which are analog, from the airflow sensing device ASD. The data acquisition interface ACQ converts these signals into a stream of upstream pressure samples PU and a stream of throat pressure samples PT, respectively, which are digital. The data acquisition interface ACQ further receives an ambient pressure signal AP from the ambient pressure sensor APS. The data acquisition interface ACQ converts this signal, which is analog and represents the ambient pressure, into a stream of ambient pressure samples PA, which are digital.

The data acquisition interface ACQ may receive a clock signal CLK from the processor PRC in order to carry out these analog to digital conversions. The upstream pressure signal UP and the throat pressure signal TP can be sampled at a relatively low rate in the order of, for example, 10 Hz. The sample streams PT, PU resulting therefrom have a corresponding rate. The ambient pressure signal AP can be sampled at an even lower rate. Such low sample rates allow low power consumption and thus long-lasting battery operation.

The processor PRC establishes data relating to respiratory characteristics of the patient on the basis of the aforementioned sample streams PT, PU, PA, which the data acquisition interface ACQ provides. This respiratory data may relate to variations of one or more respiratory parameters, which may be of statistical nature. For example, the respiratory data may include hypopnea and apnea indices that indicate a number of hypopnea and apnea events, respectively, that have occurred over a given interval of time. The respiratory data may also indicate an average breathing frequency, as well as other parameters. The processor PRC may establish further data relating to, for example, compliance of the patient. The data communication interface COM allows all this data to be transferred to a data collecting entity in a wired fashion or in a wireless fashion, or both.

Figure 5:
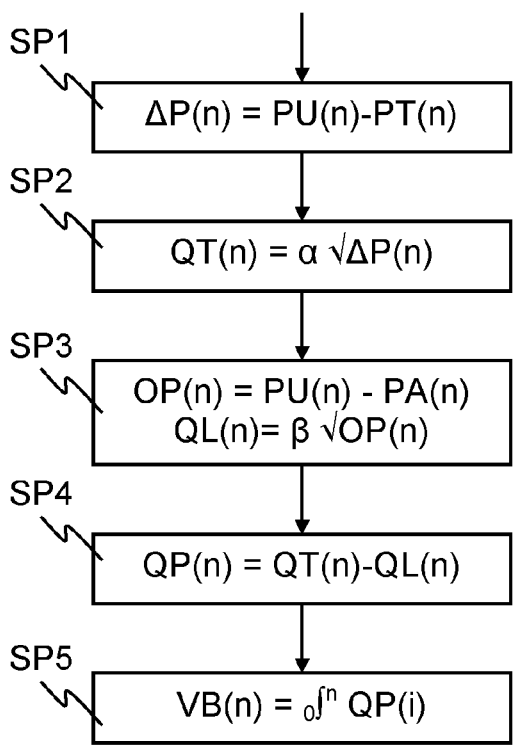
FIG. 5 is a flow chart diagram that illustrates a series of sample processing steps that forms part of a method of respiration monitoring, which can be carried out by the monitoring module.
Figure 10:
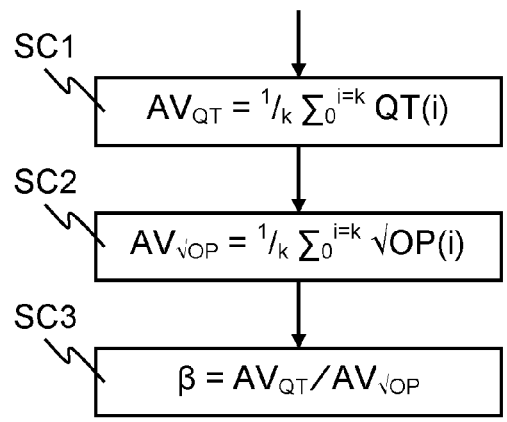
FIG. 10 is a flow chart diagram that illustrates a series of leak coefficient determination steps that forms part of the method of respiration monitoring.

FIGS. 5, 10, 11A and 11B collectively illustrate a method of respiration monitoring so as to detect, for example, hypopnea and apnea. The method comprises several series of steps that the processor PRC of the monitoring module MM carries out. FIGS. 5, 10, and 11 may thus each be regarded as flowchart representations of a set of instructions, which are stored in the program memory of the processor PRC. In general, such a set of instructions may be comprised in a computer program product that enables a processor to carry out at least a portion of the method of respiration monitoring illustrated in FIGS. 5, 10, 11A and 11B and described hereinafter. The computer program product may be in the form of, for example, a data carrier. The computer program product may be commercialized in association with an airflow sensing device, such as, for example, the airflow sensing device illustrated in FIG. 2.

FIG. 5 illustrates a series of sample processing steps SP1-SP5. The processor PRC may carry out this series of steps for a new upstream pressure sample and a new throat pressure sample that have been acquired. That is, the series of sample processing steps SP1-SP5 may repetitively be carried out at a rate corresponding to the sample rate.

In a first sample processing step SP1, the processor PRC subtracts a throat pressure sample PT(n) from an upstream pressure sample PU(n), which have preferably been acquired at substantially the same instant. This subtraction produces a pressure difference sample $\Delta P(n)$ that represents the difference between the upstream pressure and the throat pressure at this instant.

In a second sample processing step SP2, the processor PRC multiplies the square root of the pressure difference sample $\Delta P(n)$ by an airflow sensing coefficient $\alpha$. This produces a total flow rate sample QT(n) that represents an estimation of the flow rate of the airflow AF that traverses the airflow sensing device ASD at the instant concerned. The airflow sensing coefficient $\alpha$ is a predefined constant that is substantially determined by the airflow sensing device ASD, in particular by its geometrical properties. The airflow sensing coefficient a may be stored in a predefined memory location in the processor PRC, such as, for example, in a register.

It is to be noted that the estimation of the flow rate will be relatively imprecise due to the following facts. Firstly, airflow sensing devices as described hereinbefore with reference to FIGS. 2 and 3 provide relatively low Reynolds numbers in the range of flow rates between 0 and 1 liter per second, which is typical for PAP applications to which the method applies. The estimation of the flow rate will substantially be affected by a particular physical configuration and disposition of respective elements in the system illustrated in FIG. 1, such as, for example: the mask MSK, the tubes TU1, TU2, and the airflow source AFS. Secondly, difference samples ΔP are substantially affected by noise in the stream of upstream pressure samples PU and the stream of throat pressure samples PT.

In a third sample processing step SP3, the processor PRC subtracts an ambient pressure sample PA(n) from the upstream pressure sample PU(n). This subtraction produces a mask overpressure sample OP(n) that represents a difference between the pressure of the airflow AF at the mask MSK and the ambient pressure at the instant concerned. In this respect, it is recalled that the upstream pressure sample PU(n), which represents the upstream pressure, also represents the pressure of the airflow AF at the mask MSK. This is because the airflow sensing device ASD does not introduce any significant pressure loss.

The processor PRC multiplies the square root of the mask overpressure sample OP(n) by a mask leak coefficient β. This multiplication produces a leak flow rate sample QL(n) that represents an estimation of a portion of the airflow AF that leaks to the ambient air via the mask MSK. The mask leak coefficient β can dynamically be determined on the basis of upstream pressure samples PU, throat pressure samples PT, and at least one ambient pressure sample, which have previously been acquired. This will be explained in greater detail hereinafter with reference to FIG. 10.

In a fourth sample processing step SP4, the processor PRC subtracts the leak flow rate sample QL(n) from the total flow rate sample QT(n). This subtraction produces a patient flow rate sample QP(n) that represents an estimation of a flow rate of air breathed by the patient PAT at the instant concerned. The patient flow rate sample QP(n) typically has a positive value if the patient PAT breathes in and a negative value if the patient PAT breathes out. The flow rate of air breathed by the patient PAT is typically zero on average.

It is to be noted that the third and fourth sample processing steps SP3, SP4 provide a relatively precise compensation for mask leak despite imprecision in flow rate estimates. This is because the imprecision affects these estimates to the same extent. As a result, the imprecision effectively cancels out when compensating for mask leak as described with reference to FIGS. 5 and 10.

In a fifth sample processing step SP5, the processor PRC applies an integration function to a series of patient flow rate samples QP(i) (i=0, . . . , n) that have been produced thus far. The series comprises the patient flow rate sample QP(n) that has presently been produced for the instant concerned, as well as patient flow rate sample QP that have been produced for previous instants in series of sample processing steps SP1-SP5 that have previously been carried out. The integration function produces a breathed volume sample VB(n) that represents an estimation of a volume of air that the patient PAT has breathed at the instant concerned. It is to be noted that the integration operation acts as a low pass filter which smoothes out random variations due to noise in the series of patient flow rate samples. Therefore, the estimation of the volume of air breathed by the patient is relatively noise free.

FIGS. 6-9 illustrate various sample streams produced by repetitively carrying out the series of sample processing steps SP1-SP5 described hereinbefore. Each figure is in the form of a graph that has a horizontal axis, which represents time, and a vertical axis, which represents sample value.

Figure 6:
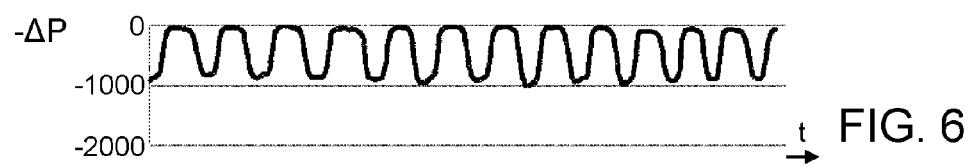
FIGS. 6-9 are signal diagrams that illustrate various sample streams produced by the series of sample processing steps.
Figure 7:
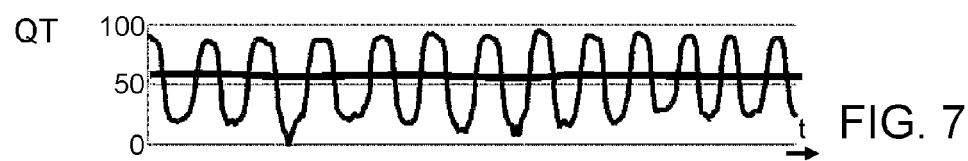

FIG. 6 illustrates a stream of pressure inverse difference samples −ΔP, which represents variations over time in the difference between the throat pressure and the upstream pressure in the airflow sensing device ASD. Sample values are expressed in units of Pascal. FIG. 7 illustrates a stream of total flow rate samples QT, which represents variations over time in estimations of the flow rate of the airflow AF that traverses the airflow sensing device ASD. Sample values are expressed in units of liters per minute. The stream of total flow rate samples QT illustrated in FIG. 7 is obtained by applying the second sample processing step SP2 described hereinbefore to the pressure difference samples of which the inverse −ΔP is illustrated in FIG. 6.

Figure 8:
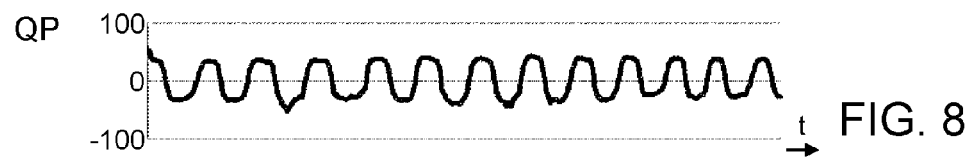
Figure 9:
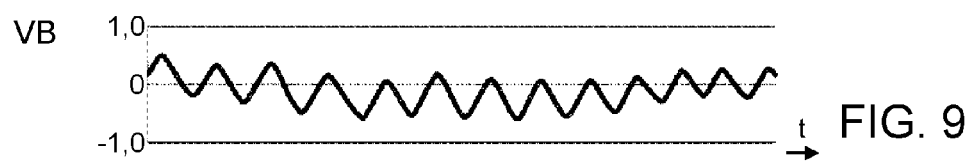

FIG. 8 illustrates a stream of patient flow rate samples QP, which represents variations over time in estimations of the flow rate of air breathed by the patient PAT. Sample values are expressed in units of liters per minute. The stream of patient flow rate samples QP illustrated in FIG. 8 is obtained by applying the third and the fourth sample processing steps SP3, SP4 described hereinbefore to the total flow rate samples QT illustrated in FIG. 7. FIG. 9 illustrates a stream of breathed volume samples VB, which represents variations over time in estimations of the volume of air that the patient PAT has breathed. Sample values are expressed in units of liters. The stream of breathed volume samples VB illustrated in FIG. 9 is obtained by applying the fifth sample processing step SP5 described hereinbefore to the patient flow rate samples QP illustrated in FIG. 8.

FIG. 10 illustrates a series of mask leak coefficient determination steps SC1-SC3. The processor PRC may repetitively carry out this series of steps at a rate that is significantly lower than the rate at which the sample processing steps SP1-SP5 are carried out. For example, the series of mask leak coefficient determination steps SC1-SC3 may be carried out at a typical respiration rate, every few seconds, or even at a slower rate.

In a first mask leak coefficient determination step SC1, the processor PRC calculates an average of total flow rate samples QT over a time interval that preferably covers several breathing cycles ($AV_{QT}=1/k\Sigma_0^{i=k}QT(i)$). This average provides an indication of the portion of the airflow AF that, on average, has leaked to the ambient air via the mask MSK over the interval of time.

In a second mask leak coefficient determination step SC2, the processor PRC calculates an average of the square root of mask overpressure samples OP over the same interval of time ($AV_{\sqrt{OP}}=1/k\Sigma_0^{i=k}\sqrt{OP(i)}$). As mentioned hereinbefore with respect to the third sample processing step SP3, a mask overpressure sample OP(n) is obtained by subtracting an ambient pressure sample PA(n) from the upstream pressure sample PU(n). The mask overpressure sample OP(n) represents an overpressure at the mask MSK at a given instant.

In a third mask leak coefficient determination step SC3, the processor PRC divides the average of total flow rate samples QT by the average of the square root of mask overpressure samples OP ($\beta=AV_{QT}/AV_{\sqrt{OP}}$). This division produces the mask leak coefficient β that will be applied in the third sample processing step SP3 until the series of mask leak coefficient determination steps SC1-SC3 is carried out anew. In other words, the mask leak coefficient β can be updated by carrying out anew the aforementioned series of steps.

Figure 11A:
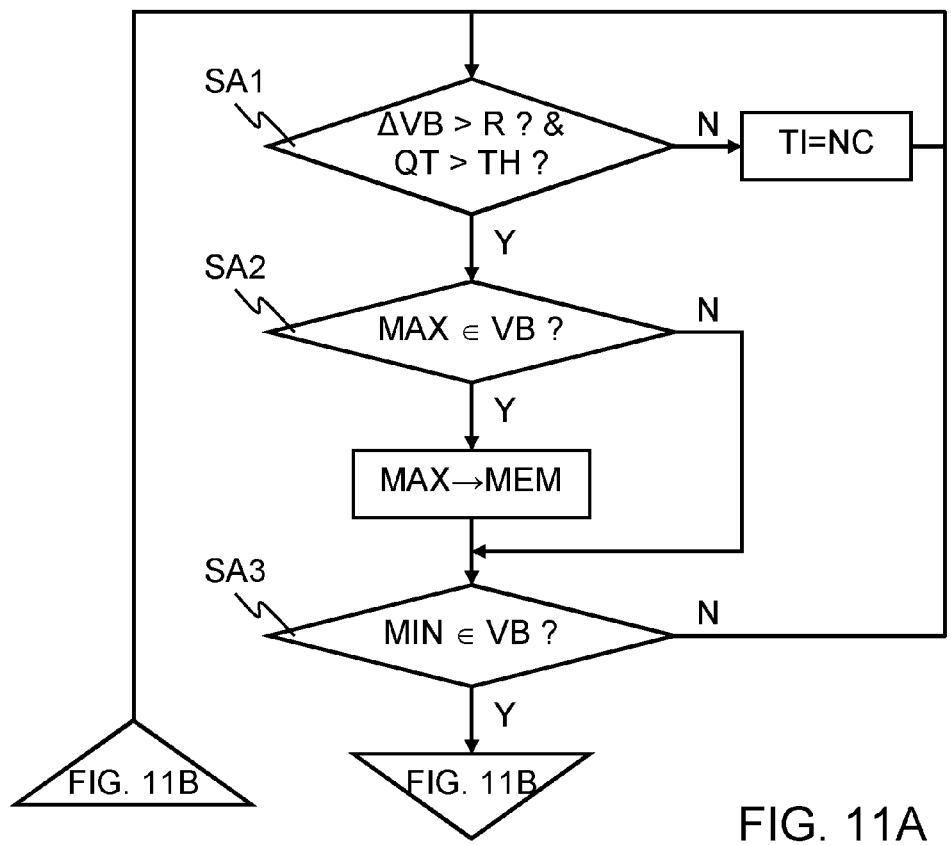
FIGS. 11A, 11B are flow chart diagrams that collectively illustrate a series of data analysis steps that forms part of the method of respiration monitoring.
Figure 11B:
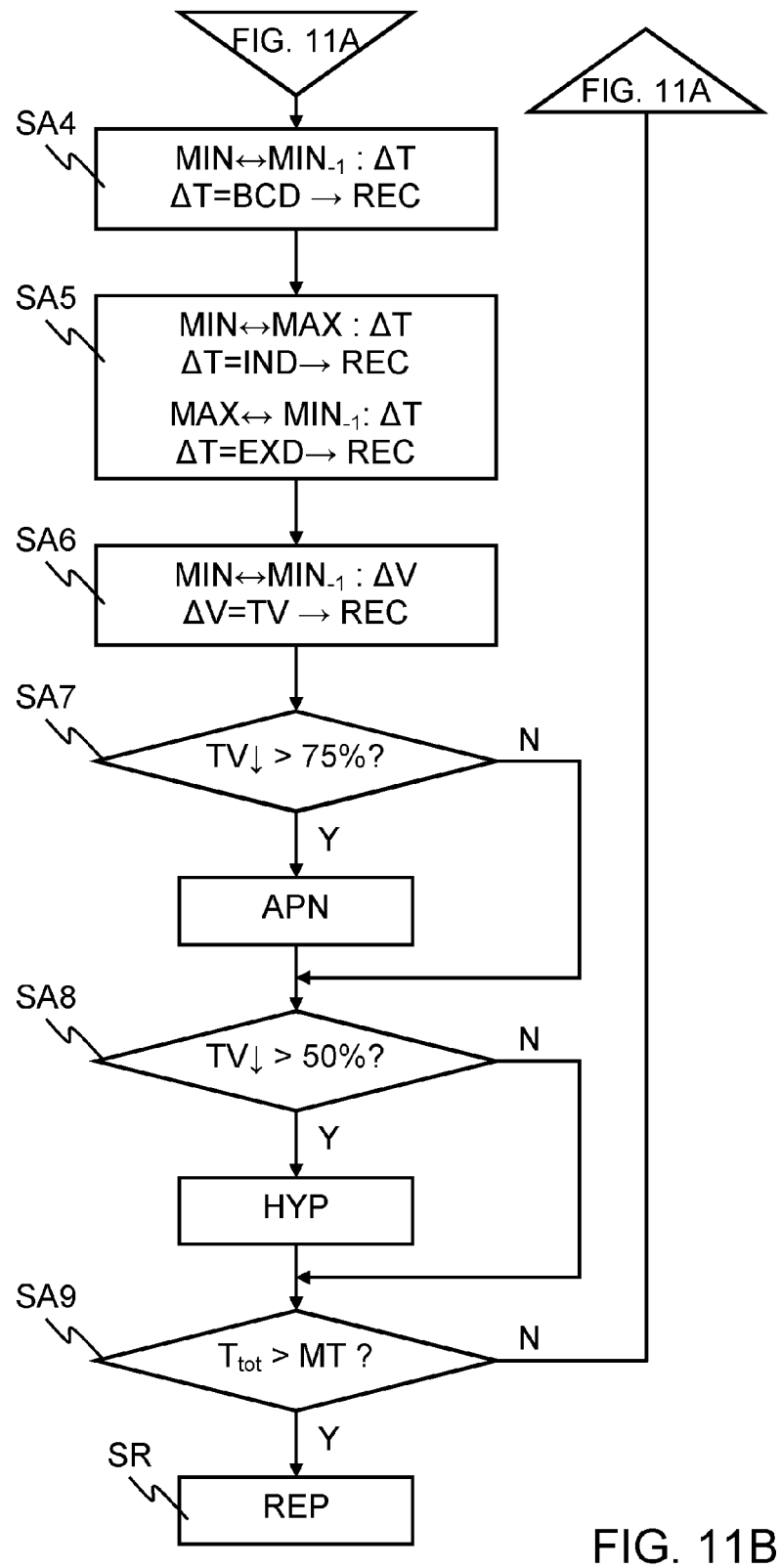

FIGS. 11A, 11B collectively illustrate a series of data analysis steps SA1-SA9 followed by a data report step SR. The processor PRC carries out these steps in association with the series of sample processing steps SP1-SP5. The processor PRC may repetitively carry out the series of data analysis steps SA1-SA9 at a rate is lower than that at which breathed volume samples VB are produced. The rate at which the series of data analysis steps SA1-SA9 is carried out, is preferably above a typical minimum breathing cycle rate.

In a first data analysis step SA1, the processor PRC checks whether the following condition is true or false: a series of breathed volume samples VB that have most recently been produced exhibits a variation that exceeds a predefined range ($\Delta$VB>R?). The series of breathed volume samples VB cover a recent time interval of given length. In addition, the processor PRC checks whether the following condition is true or false: a series of total flow rate samples QT that pertain to the same recent time interval has respective values above a given threshold (QT>TH?). In case the aforementioned conditions are both true, the recent time interval qualifies as a time interval of observance. In that case, the processor PRC subsequently carries out a second data analysis step SA2. In case any of the aforementioned conditions is false, the recent time interval qualifies as a time interval of non-observance. The processor PRC may then carry out the first data analysis step SA1 anew after a new series breathed volume samples VB have been produced.

In the second data analysis step SA2, the processor PRC checks whether the following condition is true or false: the series of breathed volume samples VB that have most recently been produced exhibits a maximum (MAX$\in$VB?). A maximum characterizes a transition from inspiration to expiration. In case the aforementioned condition is true, the processor PRC stores the instant when the maximum occurs, as well as the value of the maximum (MAX$\rightarrow$MEM). Thereafter, the processor PRC carries out a third data analysis step SA3. In case the condition is false, the processor PRC directly carries the third data analysis step SA3.

In the third data analysis step SA3, the processor PRC checks whether the following condition is true or false: a series of breathed volume samples VB that have most recently been produced exhibits a minimum (MIN$\in$VB?). A minimum characterizes a transition from expiration to inspiration. Consequently, a minimum characterizes the end of a breathing cycle and the beginning of a new breathing cycle. In case the aforementioned condition is true, the processor PRC stores the instant when the minimum occurs, as well as the value of the minimum. In case the condition is false, the processor PRC carries out the first data analysis step SA1 anew after a new series breathed volume samples VB have been produced. In case the condition is true, the processor PRC carries out a fourth data analysis step SA4.

In the fourth data analysis step SA4, which is illustrated in FIG. 11B, the processor PRC determines a time interval that has elapsed between the minimum that has been identified in the preceding third data analysis step SA3, and the most recent minimum that has been identified in the past (MIN$\leftrightarrow$MIN$_{-1}$: $\Delta$T). This time interval constitutes a breathing cycle duration BCD: the duration of the most recent breathing cycle of the patient PAT. The processor PRC stores the breathing cycle duration BCD in a record that comprises respective entries for respective breathing cycles ($\Delta$T=BCD$\rightarrow$REC).

In a fifth data analysis step SA5, the processor PRC determines a time interval that has elapsed between the minimum that has been identified in the preceding third data analysis step SA3, and the most recent maximum that has been identified (MIN$\leftrightarrow$MAX: $\Delta$T). This time interval constitutes an expiration duration EXD in the most recent breathing cycle. The processor PRC determines a further time interval that has elapsed between the most recent maximum and the most recent minimum that have been identified in the past (MAX$\leftrightarrow$MIN$_{-1}$: $\Delta$T). This time interval constitutes an inspiration duration IND in the most recent breathing cycle. The processor PRC stores the inspiration duration IND and the expiration duration EXD in the aforementioned record ($\Delta$T=IND$\rightarrow$REC; $\Delta$T=EXD$\rightarrow$REC).

In a sixth data analysis step SA6, the processor PRC determines a difference in value between the minimum that has been identified in the preceding third data analysis step SA3 and the most recent maximum that has been identified the past (MIN$\leftrightarrow$MIN$_{-1}$: $\Delta$V). This difference constitutes a tidal volume TV of the most recent breathing cycle. The processor PRC stores the tidal volume TV in the aforementioned record ($\Delta$V=TV$\rightarrow$REC).

In a seventh data analysis step SA7, the processor PRC checks whether the following condition is true or false: a reduction in tidal volume TV of more than 75% has occurred in a predefined time window that ends with the most recent breathing cycle (TV$\downarrow$>75%?). The predefined time window may be, for example, 10 seconds. In case the aforementioned condition is true, the processor PRC counts this as an apnea event (APN). Accordingly, the processor PRC may increment an apnea event counter by one unit. The processor PRC may further cause the data communication interface COM to instantaneously signal the apnea event. Thereafter, the processor PRC may carry out a ninth data analysis step SA9. In case the aforementioned condition is false, the processor PRC carries out an eighth data analysis step SA8.

In the eighth data analysis step SA8, the processor PRC checks whether the following condition is true or false: a reduction in tidal volume TV of more than 50% has occurred in the predefined time window (TV$\downarrow$>50%?). In case the aforementioned condition is true, the processor PRC counts this as an hypopnea event (HYP). Accordingly, the processor PRC may increment an hypopnea event counter by one unit. The processor PRC may further cause the data communication interface COM to instantaneously signal the hypopnea event.

In the ninth data analysis step SA9, the processor PRC checks whether the following condition is true or false: a monitoring time interval has elapsed (T$_{tot}$>MT?). The monitoring time interval may have a duration of, for example, 20 minutes. In case the aforementioned condition is true, the processor PRC carries out the data report step SR. In case the condition is false, the processor PRC carries out the first data analysis step SA1 anew.

Figure 12:
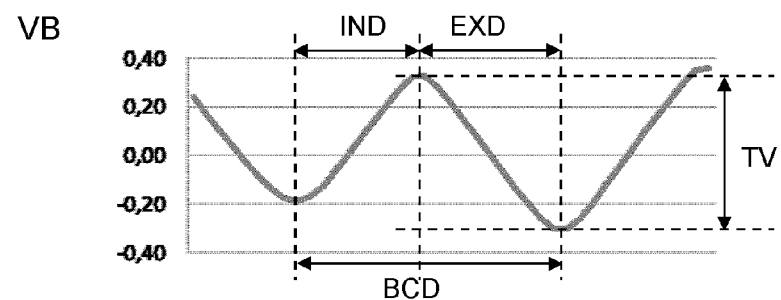
FIG. 12 is a signal diagram that illustrates a sequence of breathed volume samples from which various respiratory parameters are determined by means of data analysis steps.

FIG. 12 illustrates various respiratory parameters that are determined from a sequence breathed volume samples VB by means of various data analysis steps SA1-SA9 described hereinbefore. The sequence of breathed volume samples VB covers a breathing cycle and may correspond to a portion of the graph illustrated in FIG. 9. FIG. 12 indicates the breathing cycle duration BCD, the inspiration duration IND, the expiration duration EXD, and the tidal volume TV of the breathing cycle.

In the data report step SR, which is illustrated in FIG. 11B, the processor PRC determines the number of apnea events and the number of hypopnea events that have occurred in the monitoring time interval. The processor PRC divides the respective numbers by the duration of the monitoring time interval. These divisions produce an apnea index and a hypopnea index, respectively. The processor PRC includes these indices in a monitoring data report (REP).

The processor PRC may further accumulate all time intervals of non-observance so as to determine a total duration of non-observance and a complementary duration of observance. The latter duration should be at least equal to a duration that a physician has prescribed. The processor PRC may divide the total duration of non-observance by the duration of the monitoring time interval so as to determine a percentage of time of nonobservance. This percentage may be included in the monitoring data report.

The processor PRC may further determine a number of breathing cycles that have been detected and divide this number by the duration of the predefined monitoring time interval from which the total duration of non-observance can be subtracted. This produces an average breathing frequency, which may be included in the monitoring data report. The processor PRC may further determine an average ratio of inspiration duration IND over expiration duration EXD, and include this average ratio in the monitoring data report.

The processor PRC may determine yet further data and include this data in the monitoring data report. For example, further data may relate to significant variations in mask leak coefficients β that have been determined during the monitoring time interval. In case one or more mask leak coefficients β are outside a typical value range, which represents intentional leak, the further data may indicate the same.

At the end of the data report step SR, the processor PRC typically causes the data communication interface COM to transfer the monitoring data report to a data collecting entity.

FINAL REMARKS

The detailed description hereinbefore with reference to the drawings is merely an illustration of the invention and the additional features, which are defined in the claims. The invention can be implemented in numerous different ways. In order to illustrate this, some alternatives are briefly indicated.

The invention may be applied to advantage in numerous types of products or methods related to respiration monitoring. Respiratory parameters mentioned in the detailed description constitute examples. Variations in other respiratory parameters may equally be monitored in accordance with the invention.

There are numerous ways of implementing an airflow path according to the invention. The initial portion of the increase in diameter need not necessarily be in the form of a linear slope. The initial portion may comprise, for example, a convex or a concave form, or any other form that provides a nonlinear increase in diameter. As another example, the increase in diameter need not necessarily end with a steep portion. That is, the increase in diameter may entirely be gradual.

There are numerous ways of implementing a pressure measurement arrangement. For example, referring to FIG. 2, the upstream pressure sensor PS1 and the throat pressure sensor PS2 may be replaced by a single differential pressure sensor. One port of the differential pressure sensor may be located in the throat section T; another port may be located in the input section IN. In such an implementation, the airflow sensing device ASD will provide an output signal that represents a pressure difference. The first sample processing step SP1 described hereinbefore may then be eliminated.

There are numerous ways of implementing a monitoring module. For example, a monitoring module need not necessarily comprise an ambient pressure sensor. Referring to FIG. 2, the upstream pressure sensor PS1 can be used for measuring ambient pressure in a time interval when the airflow sensing device ASD is not used for patient monitoring and exposed to ambient air. The processor PRC illustrated in FIG. 4 may be programmed to detect such a time interval and to interpret an upstream pressure sample as being representative of ambient air pressure. Such a measurement can be relatively reliable because ambient air pressure varies relatively slowly.

There are numerous different ways of processing signals from an airflow sensing device in accordance with the invention and analyzing the data obtained therefrom. For example, data need not necessarily be analyzed "on the fly" as described hereinbefore. It is possible to store data representing processed signals for an entire monitoring session and then analyze this data once the session has ended. It should be noted that the processing of signals and the analysis of data described in this specification need not necessarily be applied in conjunction with the airflow sensing device as defined hereinbefore. Moreover, it should be noted that the processing of signals may be done, at least partially, by means of analog circuitry. For example, an analog circuit may carry out one or more particular operations that have been described with reference to FIGS. 5, 10, 11A and 11B.

It should further be noted that the sample processing steps SP1-SP5 described hereinbefore are particularly advantageous in case the airflow source AFS illustrated in FIG. 1 is of the BiPAP type. In case the airflow source AFS is of the CPAP type, a mask leak flow rate can be established in a simpler fashion. Since such an airflow source provides an airflow of constant pressure, a mask leak flow rate can be assumed to be equal to an average of the total flow rate over a recent past. Referring to the series of sample processing steps SP1-SP5 illustrated in FIG. 5, it is also possible to carry out the third sample processing step SP3 at a significantly lower rate in case the airflow source AFS is of the CPAP type.

The term "mask" should be understood in a broad sense. The term embraces any type of device capable of applying an airflow to a patient, whereby a portion of the airflow leaks to ambient air.

Although a drawing shows different functional entities as different blocks, this by no means excludes implementations in which a single entity carries out several functions, or in which several entities carry out a single function. In this respect, the drawings are very diagrammatic. For example, referring to FIG. 4, the processor PRC, the data acquisition interface ACQ, and the data communication interface COM, may form part of a single integrated circuit.

Operations may be implemented by means of hardware or software, or a combination of both. A description of a software-based implementation does not exclude a hardware-based implementation, and vice versa. Hybrid implementations, which comprise one or more dedicated circuits as well as one or more suitably programmed processors, are also possible. For example, various operations described hereinbefore with reference to FIGS. 5, 10, 11A and 11B may be carried out by one or more dedicated circuits, each of which has a particular topology that defines the operations concerned.

The remarks made herein before demonstrate that the detailed description with reference to the drawings, illustrate rather than limit the invention. There are numerous alternatives, which fall within the scope of the appended claims. Any reference sign in a claim should not be construed as limiting the claim. The word "comprising" does not exclude the presence of other elements or steps than those listed in a claim. The word "a" or "an" preceding an element or step does not exclude the presence of a plurality of such elements or steps. The mere fact that respective dependent claims define respective additional features, does not exclude a combination of additional features, which corresponds to a combination of dependent claims.

The invention claimed is:

1. A device for monitoring respiration of a patient in a system wherein an airflow source delivers a pressurized airflow and the patient receives the pressurized airflow via a mask, the device comprising:
   an airflow sensing module arranged to derive an airflow indication from the pressurized airflow, the airflow sensing module comprising:
      an inlet for receiving the pressurized airflow from the airflow source;
      an outlet for applying the pressurized airflow to the mask;
      an airflow path extending from the inlet to the outlet of the airflow sensing module, the airflow path having an axis and exhibiting a decrease in diameter followed by an increase in diameter in a direction from the inlet to the outlet, whereby the increase in diameter comprises an initial portion in which the diameter increases according to a slope of less than 10° with respect to the axis, the initial portion accounting for at least two thirds of the increase in diameter;
      a differential pressure measurement arrangement arranged to provide an indication of a pressure difference in the pressurized airflow between two sections of the airflow path within the airflow sensing module that have different diameters, the indication of the pressure difference constituting the airflow indication; and
   a processing module arranged to determine a variation of a respiratory parameter over time on the basis of successive airflow indications provided by the airflow sensing module.

2. A device according to claim 1, wherein the airflow path has a diameter profile corresponding to that of a Venturi tube.

3. A device according to claim 1, wherein the increase in diameter comprises a steep portion after the initial portion, the steep portion having a slope that is steeper than that of the initial portion.

4. A device according to claim 1, wherein the airflow path comprises a section of constant diameter between the decrease in diameter and the increase in diameter.

5. A device according to claim 4, wherein the section of constant diameter has a length corresponding to the constant diameter.

6. A device according to claim 4, wherein the differential pressure measurement arrangement is arranged to provide an indication of the pressure difference in the pressurized airflow between the section of constant diameter and an input section located before the decrease in diameter.

7. A device according to claim 6, wherein the differential pressure measurement arrangement comprises a first pressure sensor located at the input section before the decrease in diameter, and a second pressure sensor at the section of constant diameter.

8. A system for monitoring respiration of a patient, the system comprising:
   an airflow source for delivering a pressurized airflow;
   a mask for applying the pressurized airflow to the patient;
   an airflow sensing module arranged to derive an airflow indication from the pressurized airflow, the airflow sensing module comprising:
      an inlet coupled to the airflow source;
      an outlet coupled to the mask:
      an airflow path extending from the inlet to the outlet of the airflow sensing module, the airflow path having an axis and exhibiting a decrease in diameter followed by an increase in diameter in a direction from the inlet to the outlet, whereby the increase in diameter comprises an initial portion in which the diameter increases according to a slope of less than 10° with respect to the axis, the initial portion accounting for at least two thirds of the increase in diameter;
      a differential pressure measurement arrangement arranged to provide an indication of a pressure difference in the pressurized airflow between two sections of the airflow path within the airflow sensing module that have different diameters, the indication of the pressure difference constituting the airflow indication; and
   a processing module arranged to determine a variation of a volume of air breathed by the patient on the basis of successive airflow indications provided by the airflow sensing module.

9. A system according to claim 8, the processing module being arranged to carry out the following steps:
   a patient flow rate determination step in which an estimation of the flow rate of air breathed by the patient is determined on the basis of the airflow indication provided by the airflow sensing module; and
   an integration step in which an integration operation is applied to successive estimations of the flow rate of air breathed by the patient so as to obtain the estimation of the volume of air breathed by the patient.

10. A system according to claim 9, the processing module being arranged to carry out the following sub-steps as part of the flow rate determining step:
    a square-rooting sub-step in which a square root function is applied to the airflow indication provided by the the airflow sensing module so as to determine an estimation of the flow rate of the pressurized airflow through the device;
    a leak estimation sub step in which a flow rate of air that leaks from the mask is estimated; and
    a correction sub-step in which the flow rate that has been estimated is subtracted from the estimation of the flow rate of the pressurized airflow through the device so as to determine the estimation of the flow rate of air breathed by the patient.

11. A system according to claim 10, the processing module being arranged to carry out:
    a series of leak coefficient determination steps in which an average of the estimation of the flow rate of the pressurized airflow through the device is divided by an average of the square root of a difference between an estimated pressure at the mask and an ambient pressure, which division provides a mask leak coefficient, whereby, in the leak estimation sub step, the mask leak coefficient is multiplied by the square root of a difference between an estimated pressure at the mask and an ambient pressure, which multiplication provides an estimation of a flow rate of air that leaks from the mask.

12. A system according to claim 11, the system comprising an auxiliary pressure measurement arrangement arranged to provide an indication of the ambient pressure.

13. A system according to claim 8, the processing module being arranged to carry out the following steps:
    a tidal volume determination step in which a difference between a maximum and a minimum of the estimation of the volume of air breathed by the patient in a breathing cycle is determined, the difference representing an estimation of a tidal volume of the breathing cycle;

a monitoring step in which changes in successive estimations of tidal volumes of successive breathing cycles are determined so as to detect the least one of the following: hypopnea and apnea.

14. A method of monitoring respiration of a patient comprising:

a monitoring preparation step in which an inlet of an airflow sensing module is coupled to an airflow source arranged to deliver a pressurized airflow, and in which an outlet is coupled to a mask for applying the pressurized airflow to the patient; the airflow sensing module being arranged to derive an airflow indication from the pressurized airflow, the airflow sensing module comprising:

an airflow path extending from the inlet to the outlet of the airflow sensing module, the airflow path having an axis and exhibiting a decrease in diameter followed by an increase in diameter in a direction from the inlet to the outlet, whereby the increase in diameter comprises an initial portion in which the diameter increases according to a slope of less than 10° with respect to the axis, the initial portion accounting for at least two thirds of the increase in diameter; and a differential pressure measurement arrangement arranged to provide an indication of a pressure difference in the pressurized airflow between two sections of the airflow path within the airflow sensing module that have different diameters, the indication of the pressure difference constituting the airflow indication; and a monitoring execution step in which a variation of a respiratory parameter over time is determined on the basis of successive airflow indications provided by the airflow sensing module.

15. A computer program product for a device for monitoring respiration of a patient in a system wherein an airflow source delivers a pressurized airflow and the patient receives the pressurized airflow via a mask, the device comprising:

an airflow sensing module arranged to derive an airflow indication from the pressurized airflow, the airflow sensing module comprising:

an inlet for receiving the pressurized airflow from the airflow source;

an outlet for applying the pressurized airflow to the mask;

an airflow path extending from the inlet to the outlet of the airflow sensing module, the airflow path having an axis and exhibiting a decrease in diameter followed by an increase in diameter in a direction from the inlet to the outlet, whereby the increase in diameter comprises an initial portion in which the diameter increases according to a slope of less than 10° with respect to the axis, the initial portion accounting for at least two thirds of the increase in diameter;

a differential pressure measurement arrangement arranged to provide an indication of a pressure difference in the pressurized airflow between two sections of the airflow path within the airflow sensing module that have different diameters, the indication of the pressure difference constituting the airflow indication, the computer program product comprising a set of instructions that enables a processing module in the device to carry out.

a monitoring execution step in which a variation of a respiratory parameter over time is determined on the basis of successive airflow indications provided by the airflow sensing module.

* * * * *